United States Patent [19]

Berthold et al.

[11] 3,981,731

[45] Sept. 21, 1976

[54] STABILIZATION OF DEVELOPED PHOTOGRAPHIC IMAGES

[75] Inventors: Werner Berthold; Anita von König, both of Leverkusen; Helmut Timmler, Wuppertal, all of Germany

[73] Assignee: AGFA-Gevaert, A.G., Leverkusen, Germany

[22] Filed: Nov. 4, 1975

[21] Appl. No.: 628,660

[30] Foreign Application Priority Data

Nov. 9, 1974 Germany............................ 2453218

[52] U.S. Cl. ................................ 96/50 R; 96/61 R; 96/95
[51] Int. Cl.[2] ...................... G03C 5/26; G03C 5/38; G03C 1/06
[58] Field of Search .............. 96/50, 61 R, 66 R, 95, 96/109

[56] References Cited

UNITED STATES PATENTS

| | | | |
|---|---|---|---|
| 3,623,872 | 11/1971 | Berthold et al. ..................... | 96/61 R |
| 3,647,451 | 3/1972 | von Konig............................ | 96/66 R |
| 3,718,468 | 2/1973 | Berthold et al. ..................... | 96/61 R |

*Primary Examiner*—Mary F. Kelley
*Attorney, Agent, or Firm*—Connolly and Hutz

[57] ABSTRACT

Photographic images are produced by imagewise exposure, development and stabilization in which development is carried out in the presence of an $\alpha,\alpha'$-[2,5-dimercapto-1,2,4-triazolyl-4-imino]-p-xylene compound which improves the stability of the silver image in extreme climatic conditions.

6 Claims, No Drawings

STABILIZATION OF DEVELOPED PHOTOGRAPHIC IMAGES

This invention relates to a process for the production of photographic images by exposure, development and stabilization, in which development is carried out in the presence of an $\alpha,\alpha'$-bis[2,5-dimercapto-1,2,4-triazolyl-4-imino]-p-xylene compound which improves the stability of the silver image particularly where the material is to be subjected to prolonged storage under extreme climatic conditions.

In photographic high speed reproduction, it is known to stabilize developed photographic copies by means of complex forming compounds instead of the conventional method of fixing with sodium thiosulphate followed by washing. This method of stabilization differs from that of fixing with sodium thiosulphate in that the silver salts are, for the most part, left in the unexposed and undeveloped parts of the layer in the form of a light insensitive reaction product of the stabilizing compound and original silver halides. The stabilization of the developed photographic materials, however, still has certain disadvantages in the form in which it is at present carried out. One of these disadvantages is that practically all substances which form complexes with silver halides attack metallic silver, and therefore the photographic image, by converting it into a complex or noncomplex silver salt. This causes fading of the black areas or brown discoloration of the image silver or even complete disappearance of the silver image during storage. This happens particularly in a moist atmosphere. The developers and developer oxidation products present in the layer, in particular the oxidation products of hydroquinone, also reduce the stability of the image.

It is known that the stability of the image can be improved by the addition of sulphite or bisulphite compounds such as sodium sulphite or potassium metabisulphite to the stabilizing bath, which normally consists of an ammonium thiocyanate solution. According to French Pat. No. 1,258,356, not only normal sulphites and bisulphites but also their addition compounds with aldehydes or ketones may be used. A further improvement is obtained with the cyclic ketone bisulphite addition compounds described in U.S. Pat. No. 3,615,514, which are used for the same purpose.

It is also known that fading of the black areas can be prevented by the addition of heterocyclic mercapto compounds to the stabilizer solution, for example 1-phenyl-5-mercaptotetrazole as described in Belgian Pat. No. 639,140 and French Pat. No. 1,373,500 or 5-imino-3-thiourazole as described in German Auslegeschrift No. 1,299,221. Although these known compounds provide some improvement, they are not sufficiently effective in all cases. Many of the heterocyclic compounds do not have a sufficient stabilizing effect on the colour of the silver image, while others are insufficiently soluble in the aqueous acid media required for the stabilizing baths to be obtainable in the necessary concentrations. Some of the compounds produce a cloudiness or even a precipitate in the stabilizer solution so that they cannot be used over a long period. The photographic materials processed in these baths eventually contaminate the stabilizer baths with a certain concentration of silver ions which presumably have the effect of continuously reducing the activity of the added heterocyclic compound in the stabilizer solutions.

The compounds normally used in the stabilizer solutions cannot be added to the emulsion in the necessary quantities because they would inhibit development.

If the stabilizers are to be added to the emulsion, it is customary to use compounds which are not decomposed to mercapto compounds until they enter the photographic alkaline processing solution. These compounds, however, are also of restricted application since they cannot be added to the emulsion in sufficient quantities to improve sufficiently the stability of the stabilized image during prolonged storage under extreme climatic conditions.

It is also known that certain heterocyclic mercapto compounds may be added to the activator solution used for development in order to improve the stability of the silver image after it has been stabilized with a stabilizer solution containing e.g. ammoniumthiocyanate as stabilizing agent. Information about these compounds may be found in U.S. Pat. Nos. 3,623,872 and 3,718,468. The compounds described in these U.S. Patents are mainly heterocyclic compounds which contain dimercapto groups or carboxyl groups and which are sufficiently soluble in the alkaline medium of the activator solution.

For the high standards of stability sometimes demanded in photographic practice, however, these compounds do not generally have a sufficient stabilizing effect on the silver image, particularly if development of the silver image is to be followed by treatment in stabilizer baths which are required to have a hardening effect on gelatine in order to remove the tackiness of the processed images. Such baths usually contain aluminium salts. The considerable quantities of sulphite compounds which are usually used in stabilizer baths and considerably contribute to the increased stability of the silver image cannot be used in such cases because they inhibit the hardening effect of the aluminium salts so that the images would again become tacky. Only very small quantities of sulphite compounds may therefore be used in such cases, if at all. Moreover, these compounds produce an unpleasant odour because the pH of the stabilizer solutions must be kept lower than usual in order to prevent flocculation of the aluminium salts. In such cases, the stabilizer compounds in the activator must meet more stringent demands which cannot be adequately fulfilled by the known additives. Furthermore, the known heterocyclic compounds which contain carboxyl groups decompose when stored for several months in the strongly alkaline activator solutions and are converted into non-effective compounds. They are therefore of limited usefulness in alkaline activator solutions which must have a shelf life of several months.

In addition, some of the known compounds inhibit development and therefore reduce the maximum density as well as the sensitivity of the photographic material.

It is an object of the present invention to provide compounds which reduce or substantially obviate the disadvantages described above of the known stabilizing processes and which make it possible to obtain stabilized black silver images which remain stable even if they are stored over prolonged periods under moist, warm conditions and particularly also if stabilizer baths with hardening additives have been used for the production of the silver images.

Further object of the invention is the production of photographic images by exposure of a photographic material which contains at least one silver halide emulsion layer, development and stabilization of the unexposed and undeveloped silver halide in which development is carried out in the presence of an α,α'-bis-[2,5-dimercapto-1,2,4-triazolyl-4-imino]-p-xylene compound of the following formula or its salts:

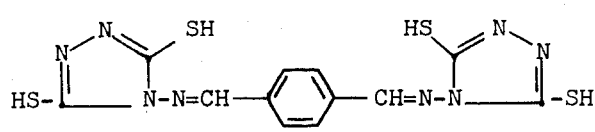

The compound is preferably prepared by reacting 2,5-dimercapto-4-amino-1,2,4-triazole with terephthalic aldehyde in dimethyl sulphoxide, for example by the following method:

6.7 of terephthalic dialdehyde (0.05 mol) and 16.3 g of 2,5-dimercapto-3-amino-1,2,4-triazole (0.11 mol) were heated in 400 ml of dimethylsulphoxide at 80°C for from 6 to 8 hours in a nitrogen atmosphere with stirring. After cooling to room temperature, the precipitate was suction filtered, washed with dimethylsulphoxide and purified by repeated addition of methylene chloride and stirring. The yield was 21.3 g, which was 98% of the theoretical yield of α,α'-bis-[2,5-dimercapto-1,2,4-triazolyl-4-imino]-p-xylene which had a melting point 246°C.

21 g of α,α'-bis-[2,5-dimercapto-1,2,4-triazolyl-4-imino]-p-xylene were dissolved in 260 ml of dimethylformamide by first heating gently and then heating to boiling for 5 minutes. After the solution had been left to cool and stand overnight, the resulting dimethylformamide salt of the compound was suction filtered, washed with ethanol and dried. The yield was 15 g and the product had a melting point of 250°–265°C, depending on the residual dimethylformamide content.

4-Amino-3,5-dimercapto-1,2,4-triazole is prepared by reacting thiocarbohydrazide with carbon disulphide in pyridine in known manner, for example as described in Acta Chemica Scandinavica 15, pages 1295–1302 (1961).

The compound according to the invention may, of course, also exist in the corresponding thion form. The compounds are preferably isolated and used as free mercapto compounds in the form of their salts, e.g. the dimethylformamide salt. The compounds according to the invention has the following advantages over the compounds described in U.S. Pat. Nos. 3,623,872 and 3,718,468:

1. The compound according to the invention can be prepared in very high yields by a very simple method. The starting materials are easily prepared or available commercially. The prior art compounds heteroalkylene-5,5'-bis-1,2,4-triazole-3-mercaptans, on the other hand, must be prepared by reacting thiosemicarbazide with carboxylic acid esters which contain thioether groups. The latter compounds, as is well known, are very difficult to handle during their preparation, not least because of their unpleasant odour, and the process of preparing them and reacting them to form the prior art stabilizing compounds is relatively expensive and, moreover, only low yields can be obtained in the necessary ring closure reaction by condensation of the ester with thiosemicarbazides.

2. The compound according to the invention can be kept for many months in the alkaline activator baths and is superior in its stability to numerous compounds known in the art.

3. Those of the prior art compounds which are easily prepared have a much weaker stabilizing effect when used in the activator baths according to the invention than the compound according to the invention and/or they have a much more harmful effect on the development of the silver image.

In contrast to the prior art compounds, the compound according to the invention has an excellent stabilizing effect on the developed silver image without any significant harmful effect on the development of the silver image. Its stabilizing effect is excellent even when it is used in relatively small quantities of about 1 g/l of activator solution, so that the addition of the compound according to the invention does not critically increase the manufacturing costs of the activator baths. Furthermore, the compound according to the invention is readily soluble in the activator baths and has no tendency to contaminate the baths in use by the formation of cloudiness or precipitates.

The compound according to the invention is therefore surprisingly superior to similar compounds which can be obtained by the condensation of other monomercapto aminotriazole or monomercapto aminothiadiazole compounds with terephthalic dialdehyde, since these prior art compounds are either insufficiently soluble in activator baths or incapable of producing more than a slight stabilizing effect if any, and what stabilizing action they do have is less than that of those other known compounds of the art.

The usual light-sensitive photographic materials which contain at least one silver halide emulsion layer may be processed by the process according to the invention. The light-sensitive emulsions may contain any silver halides, such as silver chloride or silver bromide, if desired with a small silver iodide content of up to 10 mols-%. Emulsions with a high silver chloride content are preferred, especially there wherein the silver halide consists nearly completely of silver chloride.

The binders used for the light-sensitive layers may be any of the usual water permeable film-formers, in particular proteins and preferably gelatine.

The emulsions may also contain alkylene oxide polymerisation products as chemical sensitizers. In addition, they may contain already known stabilizers. The emulsions may also contain developers or developer combinations based on hydroquinone, pyrocatechol or aminophenol or compounds based on pyrazolidone or phenylenediamino derivatives and they may contain antioxidants for the developer, e.g. potassium metabisulphite, aldehyde bisulphite and ketone bisulphite, matting agents and white toners.

Development is carried out in the usual manner, using known developer substances. According to a preferred embodiment of the invention, the developer is added to the photographic material and development is started by treating the material with an aqueous alkaline bath, hereinafter referred to as the activator bath.

The compound to be used according to the invention or its salt, e.g. with dimethylformamide, may vary within wide limits in its concentration in the bath used for development. The concentration required depends on the photographic material used and the nature of the developer. The optimum concentrations for any given reproduction process can be determined by the usual series of tests. It has usually been found satisfactory to use additions of 0.5 to 10 g/l of processing bath, preferably 1 to 3 g per liter.

Suitable stabilizers, i.e. compounds which are capable of converting the silver halide left after development into a light-insensitive compound, have been described, for example, in British Pat. Nos. 631,184 and 959,807; U.S. Pat. No. 2,525,532 and French Pat. No. 1,237,454. Ammonium thiocyanate and alkali metal thiocyanates such as sodium or potassium thiocyanate have proved to be particularly suitable.

The stabilizing baths may also contain the usual additives such as hardeners, acetic acid or its salts, sulphites such as potassium metabisulphite, aldehyde and ketone bisulphite, in particular cyclohexanone bisulphite and organic compounds such as 1-phenyl-5-mercaptotetrazole or 4-amino-3,5-dimercapto-1,2,4-triazole. Suitable hardeners are in particular aluminium salts and chromium-III salts.

EXAMPLE 1

A light-sensitive photographic material containing a silver chloride gelatine emulsion layer mounted on a substrate, which emulsion layer contains 0.2 mol of silver halide with a silver iodide content of less than 0.1 mol % per kg of emulsion (silver application 1.3 g/m$^2$) and hydroquinones (12 g of hydroquinone per kg of emulsion) was uniformly subjected to maximum exposure and developed in the following activator solution:
80 g of sodium hydroxide,
50 g of sodium sulphite secc.,
2 g of potassium bromide, made up with water to 1 liter.

The compounds shown in the following table were added to the above activator solution. The quantities added were shown in the table.

The developed material was treated with the following stabilizer solution:
1000 ml of water,
300 g of ammonium thiocyanate cryst.
30 g of cyclohexanone bisulphite,
61.2 ml of 98% glacial acetic acid,
40 g of aluminium sulphate cryst.
8 g of boric acid
50 g of sodium acetate sicc.

The samples were processed at room temeperature in a Rapidoprint two-bath development apparatus of the usual construction, model L D 37 manufactured by Agfa-Gevaert AG. The photographic material was passed through the apparatus at a uniform rate with the aid of guide rollers. It was first wetted by the activator bath for about 2 seconds and, after the liquid has been squeezed off, the material was dipped in the stabilizer bath for about 4 seconds.

To test the stability of the silver image, the developed and stabilized sample was then sealed into a water-tight bag of aluminium laminated or polyethylene laminated paper immediately after leaving the developer apparatus, while it was still moist.

The bag was then stored in a heating cupboard at 50°C and 100 % atmospheric humidity and the material was examined after storage times of 4, 8, 16, 24 and 48 hours for any change in the silver image.

The black silver image turned brown or bleached to varying degrees according to the length of storage time and the substance added. The discoloration and bleaching of the individual samples were observed to increase from the edges inwards and to be particularly pronounced in those areas of photographic material where less pressure had been applied by the squeezing rollers to remove the stabilizer solution so that the concentration of residual stabilizer in the layer remained higher.

The maximum densities of the areas which were not yet bleached in the individual samples were determined in a densitometer in the usual manner.

As can be seen from the figures in the following Table, the control sample which was not treated with additional stabilizing substance in the activator solution is completely bleached after only 24 hours under the extreme testing conditions described above. Although comparison compounds 11 and 38 from British Pat. Specification No. 1,293,622 show some effect on the stability of the silver image, it can be seen that after 24 hours' storage the sample prepared according to the invention still has a substantially higher residual density and more uniform blackening than the comparison sample. After 48 hour's storage, it is distinctly superior to the comparison example.

Compound No. 38 from British Pat. Specification No. 1,293,622 is approximately equal to the compound according to the invention in its stabilizing effect on the silver image when used in the same gram quantities, but it has the disadvantage over the compound according to the invention that, as is well known, it powerfully inhibits development in some emulsions and, moreover, it tends to form deposits and precipitates in the developer apparatus. The compound according to the invention is also distinctly superior to the compounds described in British Pat. Specification No. 1,249,277 not only in its silver stabilizing effect, as can be seen from the figures in the table, but also because in contrast to the comparison compound it remains stable for two months in activator baths without losing its effect.

Table 1

| Additive | Concentration g/l | 0 hours | Maximum density after moist warm storage for | | | | |
| --- | --- | --- | --- | --- | --- | --- | --- |
| | | | 4 hours | 8 hours | 16 hours | 24 hours | 48 hours |
| Control sample | 0 | 1.97 | 1.77 | 1.72 | 1.15 | completely bleached | |
| Compound 11 from | | | | | | onset of bleaching in parts | completely bleached |
| GB 1,293,622 | 1 | 2.00 | 1.97 | 1.96 | 1.80 | | |
| Compound 2 from | | | | | | | completely bleached |
| GB 1,249,277 | 1 | 1.97 | 1.97 | 1.89 | 1.57 | 1.19 | |
| Compound 38 from | | | | | | | 0.43 partly |
| GB 1,293,622 | 1 | 2.0 | 1.96 | 1.99 | 1.72 | 1.41 | bleached |
| Compound according to the | | | | | | | 0.79 partly |

Table 1-continued

| Additive | Concentration g/l | Maximum density after moist warm storage for | | | | |
|---|---|---|---|---|---|---|
| | | 0 hours | 4 hours | 8 hours | 16 hours | 24 hours | 48 hours |
| invention | 1 | 2.1 | 2.09 | 2.07 | 1.83 | 1.42 | bleached |

EXAMPLE 2

The procedure was the same as that described in Example 1 but a solution of the following composition was used instead of the stabilizer solution described in Example 1:
1000 ml of water,
350 g of ammonium thiocyanate cryst.
61.2 ml of 98% glacial acetic acid
40 g of aluminium sulphate cryst.
8 g of boric acid
50 g of sodium acetate.

The figures given in Table 2 below show that the control sample which was processed without any stabilizing additive in the activator was completely bleached after 24 hours' storage under moist, warm conditions.

Samples which contained compounds of the following formula as additive I and II were tested for comparison:

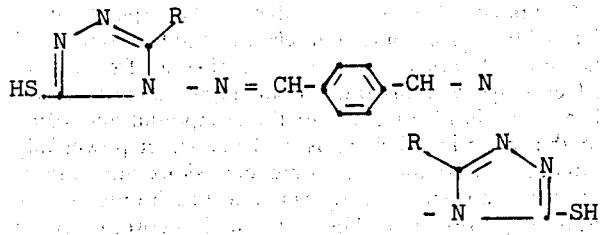

I: R = CH$_3$; II; R = C$_2$H$_5$.

The preparation of the comparison compounds is as easy to perform as that of the compounds according to the invention, but they are not suitable as stabilizers for the purpose according to the invention. The comparison samples are already partly bleached after 24 hours' storage while the sample according to the invention shows only a uniform reduction in density which does not significantly impair the impression of the image.

Table 2

| Additive | Concentration g/l | Maximum density after moist, warm storage for | | | |
|---|---|---|---|---|---|
| | | 0 hours | 4 hours | 16 hours | 24 hours |
| Control sample | 0 | 1.91 | 1.67 | 1.23 | complete bleached |
| I | 1 | 1.96 | 1.90 | 1.37 | 0.79 partly bleached |
| II | 1 | 1.93 | 1.88 | 1.43 | 0.7 partly bleached |
| Compound according to the invention | 1 | 1.98 | 1.94 | 1.58 | 1.23 |

We claim:
1. In a process for the production of photographic images by exposure of a photographic material which contains at least one silver halide emulsion layer, development and stabilization of the unexposed and undeveloped silver halide, the improvement according to which development is carried out with a bath containing a compound of the following formula or salts thereof

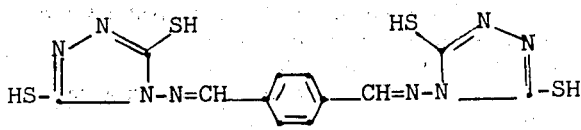

2. Process according to claim 1, in which a dimethylformamide salt of the compound is used.
3. Process according to claim 1, in which the photographic material used contains a photographic developer substance in the light sensitive silver halide emulsion layer and is developed with an aqueous alkaline bath.
4. Process according to claims 1, in which an ammonium thiocyanate stabilizing bath is used for stabilization.
5. Process according to claim 4, in which the stabilizing bath in addition contains cyclohexanone bisulphite.
6. Process according to claim 4, in which the stabilizing bath contains aluminium salts as hardener.

* * * * *